(12) United States Patent
Meckel

(10) Patent No.: US 6,330,750 B1
(45) Date of Patent: Dec. 18, 2001

(54) SCAPEL BLADE HAVING HIGH SHARPNESS AND TOUGHNESS

(75) Inventor: Nathan K. Meckel, LaMesa, CA (US)

(73) Assignee: Molecular Metallurgy, Inc., El Cajon, CA (US)

( * ) Notice: Subject to any disclaimer, the term of this patent is extended or adjusted under 35 U.S.C. 154(b) by 0 days.

(21) Appl. No.: 09/526,406

(22) Filed: Mar. 15, 2000

Related U.S. Application Data

(63) Continuation-in-part of application No. 08/909,910, filed on Aug. 12, 1997, now Pat. No. 6,076,264, which is a continuation-in-part of application No. 08/585,177, filed on Jan. 11, 1996, now Pat. No. 5,724,868.

(51) Int. Cl.[7] ........................................................ B26B 9/00
(52) U.S. Cl. ...................... 30/350; 30/346.54; 76/104.1
(58) Field of Search .......................... 30/350, 346.54, 30/346.53; 76/104.1, DIG. 8, DIG. 11, 116; 428/660, 661

(56) References Cited

U.S. PATENT DOCUMENTS

| | | | |
|---|---|---|---|
| 3,874,900 | * 4/1975 | Post et al. .......................... | 30/350 X |
| 3,911,579 | * 10/1975 | Lane et al. .......................... | 30/346.54 |
| 4,945,640 | * 8/1990 | Garg et al. .............................. | 30/350 |
| 5,256,496 | * 10/1993 | Kluczynski ........................ | 30/350 X |
| 5,669,144 | * 9/1997 | Hahn et al. ........................ | 30/346.54 |

* cited by examiner

*Primary Examiner*—Douglas Watts
(74) *Attorney, Agent, or Firm*—Nydegger & Associates

(57) ABSTRACT

A scalpel blade is made by depositing a coating onto a tapered region of a substrate which is tapered with an included angle of from about 10 to about 25 degrees to an edge. The substrate is made of surgical-grade stainless steel hardened to a Rockwell C hardness of at least 54 and then annealed to a Rockwell C hardness of from about 46 to less than about 53. The coating overlying the tapered region has a thickness of from about 0.1 to about 2.5 micrometers and includes a first coating layer of a first metal, and a second coating layer overlying the first coating layer. The first coating layer is preferably zirconium or a zirconium-base alloy, and the second coating layer is preferably zirconium nitride. The edge may be atomically sharpened by applying a large negative voltage to the substrate relative to the deposition source while a portion of the thickness of the second coating layer is being deposited.

20 Claims, 4 Drawing Sheets

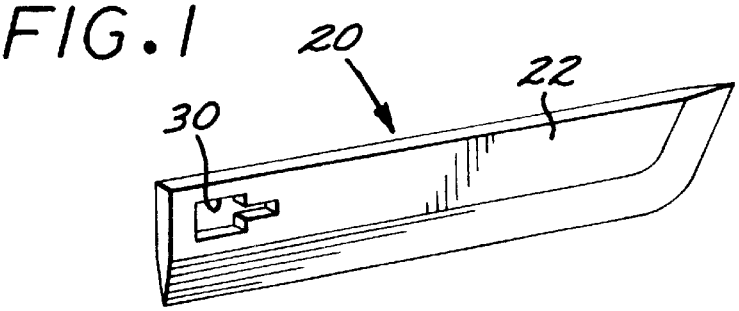
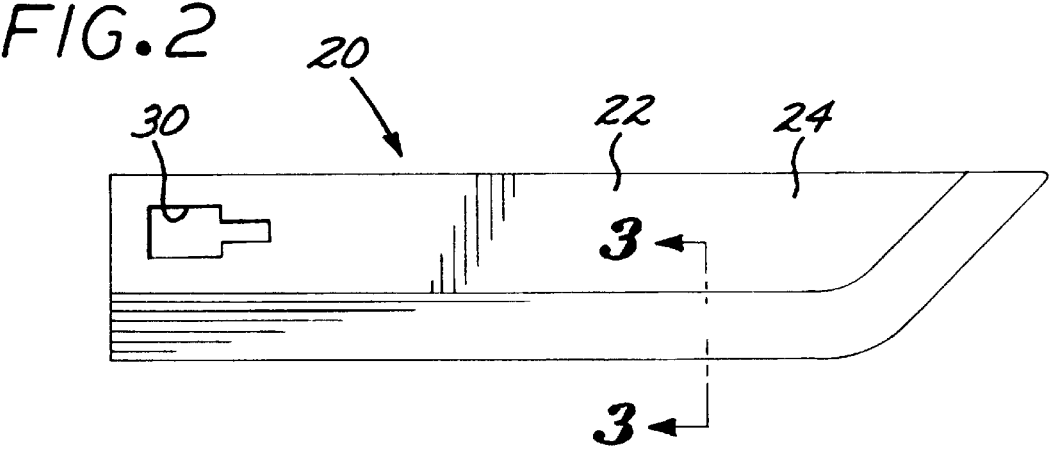
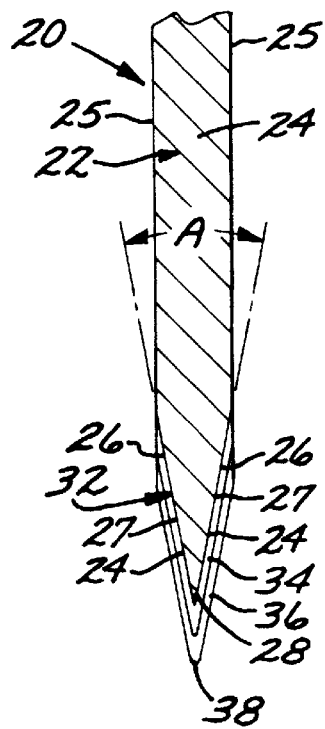

SCAPEL BLADE HAVING HIGH SHARPNESS AND TOUGHNESS

This application is a continuation-in-part of pending application Ser. No. 08/909,910, filed Aug. 12, 1997 now U.S. Pat. No. 6,076,264, which in turn is a continuation-in-part of application Ser. No. 08/585,177, filed Jan. 11, 1996, now U.S. Pat. No. 5,724,868.

This invention relates to scalpel blades and their production and, more particularly, to such blades having high toughness and a high sharpness that is retained for an extended period of use.

BACKGROUND OF THE INVENTION

A scalpel is a small knife, typically with a removable blade, that is used in medical, veterinary, biological, and other procedures to cut a workpiece. Scalpel blades used in medical, veterinary, and biological procedures must be very sharp so as to inflict as little damage as possible to the tissue being cut. They must retain that sharpness for as long as possible during a procedure to minimize the number of instrument changes during the procedure.

Conventional scalpel blades are made of a surgical grade stainless steel that is hardened to a Rockwell C hardness of about 54–62 in order to retain the sharpness of their cutting edges throughout a procedure. They are sharpened to an included blade angle that is typically about 26 degrees. It would be desirable to reduce the included blade angle so as to increase the sharpness of the scalpel blade. The result of such a reduction of the included blade angle is to increase the tendency of the blade to bend and roll over, rendering it ineffective. The blade also has a tendency to break during a procedure, because the high hardness results in a low ductility and toughness that render the very thin blade susceptible to brittle failure. Brittle failure is of particular concern during surgery because the broken piece of the scalpel blade is difficult to find and may be retained within the body of the patient. The reduction in the included blade angle of conventional scalpel blades also causes the blades to become dulled very quickly during service.

On the other hand, the stainless steel may be annealed to reduce the Rockwell C hardness to a level where the blade has reasonable toughness and a reduced tendency to brittle fracture. The result is that the tapered region of the blade still has a rollover tendency that can render it ineffective. Further, because the steel is softer and does not hold an edge as well, the service life of the sharp edge is greatly reduced so that only a few cuts may be made before the scalpel blade must be replaced.

There is a need for an improved scalpel and scalpel blade which has an increased sharpness that is retained for an extended period of time, yet is not susceptible to brittle fracture during a procedure. The present invention fulfills this need, and further provides related advantages.

SUMMARY OF THE INVENTION

The present invention provides a scalpel blade and a method for its manufacture. The scalpel blade has a high sharpness that is retained for an extended period of use in service. The scalpel blade is relatively ductile as compared with conventional scalpel blades, so that it has a reduced tendency to brittle fracture. The increased ductility also improves the consistency of performance of the scalpel blade in service. The scalpel blade of the invention is otherwise compatible with conventional scalpel blade holders and requires no changes to medical and other cutting procedures that use the scalpel blade. The manufacturing method produces scalpel blades of consistent structure and functionality.

A coated scalpel blade comprises a substrate having a body and a tapered region with an edge thereon. The tapered region desirably has an included angle of from about 10 to about 25 degrees, more preferably from about 10 to about 18 degrees. The substrate is made of steel, preferably first hardened to a Rockwell C hardness of at least 54 and then annealed back to a Rockwell C hardness of from about 46 to less than about 53. A coating overlies the tapered region. The coating has a thickness of from about 0.1 to about 2.5 micrometers, preferably from about 0.1 to about 1.0 micrometer, and most preferably about 0.3 micrometer. The coating comprises a first coating layer of a first metal, and a second coating layer overlying the first coating layer. The second coating layer comprises a chemical combination of a second metal selected from the group consisting of vanadium, chromium, zirconium, titanium, niobium, molybdenum, hafnium, tantalum, and tungsten, and combinations thereof, and a nonmetal selected from the group consisting of nitrogen and carbon, and combinations thereof. Most preferably, the first metal and the second metal are the same, and the coating has a first coating layer of zirconium and a second coating layer of zirconium nitride. The coated scalpel blade preferably has a coated edge thereon which is atomically serrated and atomically sharpened.

A method for preparing a coated scalpel blade includes the step of providing a substrate having a body and a tapered region with an edge thereon. The substrate is made of steel hardened to a Rockwell C hardness of at least 54. The substrate is thereafter annealed to reduce its hardness by at least about 5 points of Rockwell C hardness. A coating is deposited from a deposition source onto at least the tapered region of the substrate. The coating has a thickness of from about 0.1 to about 2.5 micrometers. The step of depositing comprises the steps of first depositing a first coating layer of a first metal, and thereafter second depositing a second coating layer overlying the first coating layer. The second coating layer comprises a chemical combination of a second metal selected from the group consisting of vanadium, chromium, zirconium, titanium, niobium, molybdenum, hafnium, tantalum, and tungsten, and combinations thereof, and a nonmetal selected from the group consisting of nitrogen and carbon, and combinations thereof. The step of second applying includes the step of applying a voltage more negative than about −70 volts to the substrate relative to the deposition source, in the latter portion near the end of the second applying step. This preparation process produces a scalpel blade that has excellent properties, and which are highly reproducible in production operations and yield consistent service performance.

Preferably, the step of annealing and the step of depositing are performed in the same apparatus. The deposition source is desirably a cathodic arc deposition source. The step of providing may include the step of providing a plurality of substrates, and the step of depositing includes the steps of stacking the plurality of substrates with their bodies adjacent to each other and their edges facing in a common direction, and orienting the edges facing toward the deposition source. Other features described above may be incorporated into the method.

The resulting scalpel blade is very sharp, both because it has a small included angle of the tapered region and because, in the preferred approach, it is atomically sharpened by the application of the large negative voltage toward the end of the deposition of the second coating layer. It is also relatively ductile and metallurgically tough, because the steel substrate is annealed. The presence of the coating allows the metal to be annealed and yet have the included blade angle small, because the coating strengthens the tapered region of the blade so that it resists bending and rollover of the blade more effectively. The resulting scalpel blade is tough and resistant to brittle fracture, so that there is a greatly reduced likelihood of breakage during the cutting procedure. The scalpel blade is also sharp, and it retains the sharpness for extended periods of use in service.

The structure and function of the scalpel blade are distinct from another commonly available sharp article, a razor blade. The razor blade is supported from a holder over the entire length of its cutting edge, and outwardly extends from the holder only a short distance. The scalpel blade, on the other hand, is cantilevered from its handle by a relatively large amount. The sharp end of the scalpel blade may be used for cutting, and must withstand both conventional cutting action and impacts against hard objects. It requires a substantially greater toughness than the razor blade.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 1 is perspective view of a scalpel blade;

FIG. 2 is an enlarged side elevational view of the scalpel blade of FIG. 1;

FIG. 3 is a greatly enlarged schematic sectional view of the scalpel blade of FIG. 2, taken along line 3—3;

DETAILED DESCRIPTION OF THE INVENTION

Figure 4:
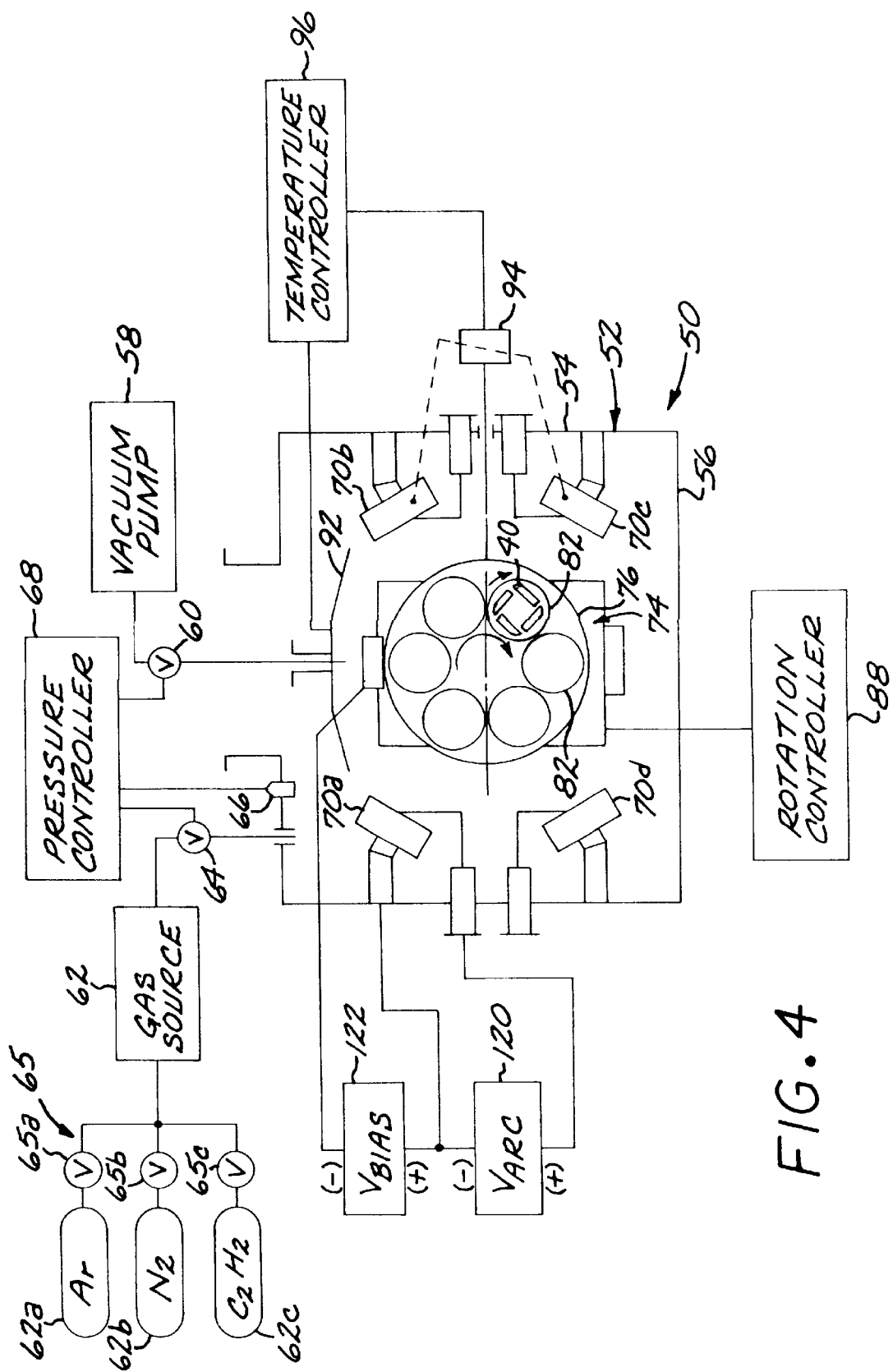
FIG. 4 is a schematic plan view and control diagram of a deposition apparatus according to the invention.

FIGS. 1–3 depict a coated scalpel blade 20. The scalpel blade 20 may be described as a substrate 22 having a body 24 with parallel sides 25 and a tapered region 26 with converging sides 27. The tapered region 26 is continuous with the body 24 and tapers to an edge 28. The tapered region 26 has an included angle A, shown in FIG. 3, of from about 10 to about 25 degrees, more preferably from about 10 to about 18 degrees. If the included angle A is less than about 10 degrees, the tapered region 26 is so thin that it has insufficient strength in service. If the included angle A is more than about 25 degrees, the scalpel blade is operable but has insufficient inherent substrate sharpness. An included angle of from about 10 to about 18 degrees yields a combination of excellent sharpness and acceptable strength, when the substrate 22 is coated in the manner described subsequently.

The substrate 22 is made of steel, preferably a stainless steel such as Type 440 stainless steel having a nominal composition in weight percent of 16–18 percent chromium, 0.6–0.75 percent carbon, maximum 1 percent manganese, maximum 0.04 percent phosphorus, maximum 1 percent silicon, maximum 0.75 percent molybdenum, maximum 0.03 percent sulfur, balance iron. The stainless steel is hardened to a Rockwell C hardness of at least 54, typically 54–62, and then annealed to reduce its Rockwell C hardness by at least about 5 points, and preferably to a Rockwell C hardness of from about 46 to less than about 53.

An aperture 30 extends through the body 24 of the substrate 22. The aperture 30 has a shape that engages a corresponding pin (not shown) in a handle (not shown) that is used to hold the scalpel blade 20 during service.

A coating 32 overlies at least a portion of the sides 27 of the tapered region 26. The coating 32 may overlie the body 24 as well, but it need not. The preferred manufacturing approach, to be described subsequently, deposits the coating 32 only over the sides 27 of the tapered region 26 and not the parallel sides 25 of the body 24.

The coating 32 comprises a first coating layer 34 of a first metal (and metallic alloys thereof, typically containing more of the first metal than any other element) that contacts and is deposited upon at least a portion of the sides 27 of the tapered region 26. A second coating layer 36 overlies the first coating layer 34. The second coating layer 36 comprises a chemical combination of a second metal selected from the group consisting of vanadium, chromium, zirconium, titanium, niobium, molybdenum, hafnium, tantalum, and tungsten, and combinations thereof, and a nonmetal selected from the group consisting of nitrogen and carbon, and combinations thereof. Preferably, the first metal is the same as the second metal.

The first coating layer 34 is present to aid in adhering the second coating layer 36 to the substrate 22, and the second coating layer 36 provides hardness, wear resistance, and cutting-edge retention to the scalpel blade 20. The two coating layers 34 and 36 in combination strengthen the tapered region 26 to allow it to be made with a small included angle A of from about 10 to about 25 degrees.

The most preferred structure of the coating 32 is the first coating layer 34 of zirconium (including metallic alloys thereof) and the second coating layer 36 of zirconium nitride. The zirconium nitride is preferred over other operable materials such as titanium nitride because the zirconium nitride is more inert, is harder, and has a greater lubricity.

The coating 32 has a thickness of from about 0.1 to about 2.5 micrometers, more preferably from about 0.1 to about 1.0 micrometers, and most preferably about 0.3 micrometers. If the coating 32 is thinner, it does not provide the required mechanical properties. If the coating is thicker in the region of the substrate edge 28, it dulls the cutting edge and has an increased tendency to spall off the substrate 22. The first coating layer 34 is quite thin, typically on the order of about 100–600 Angstroms thick, and the second coating layer 36 makes up the remainder of the thickness of the coating 32.

The coating 32 may optionally have additional layers. For example, one or more additional layers may be deposited between the first coating layer 34 and the second coating layer 36. Additional layers may be deposited overlying the second coating layer 36, but the second coating layer 36 is preferably the topmost of the layers.

The coating, having the second coating layer 36 of the hard material, preferably zirconium nitride, serves to provide lateral mechanical stabilization to the thin tapered region 26. This mechanical stabilization serves to inhibit bending and thence rollover and buckling of the tapered region 26 of the scalpel blade 20 during service. It is therefore possible to make the included angle A smaller than would otherwise be the case in the absence of the second coating layer 36. The smaller included angle A makes the scalpel blade 20 inherently sharper. The presence of the hard coating 32 itself, and the processing approach, also aid in achieving a high level of sharpness of the scalpel blade 20.

The coated scalpel blade 20 has a coated edge 38 thereon. This coated edge 38 performs the cutting action when the scalpel blade 20 is used. This coated edge 38 is quite sharp and durable. To improve the cutting action, the coated edge 38 is preferably atomically serrated and atomically sharpened along its length. The atomic-level serrations are somewhat comparable to the serrations on the cutting edge of some conventional knives, and serve the same cutting-enhancement functions, but are present on a microscopic scale. The atomically serrated and sharpened structure is produced in a manner to be described by the preferred preparation approach.

Figure 5:
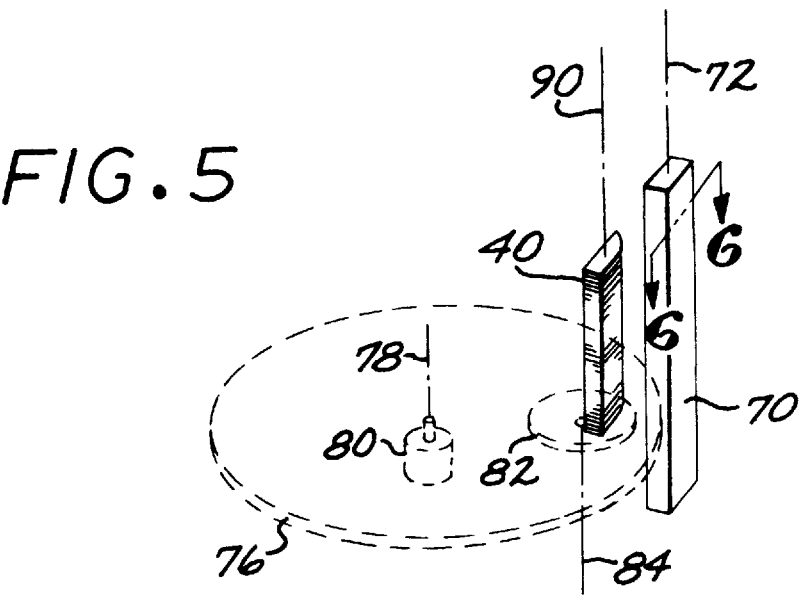
FIG. 5 is a schematic perspective view of a detail of the deposition apparatus of FIG. 4.

FIGS. 4 and 5 depict a cathodic arc deposition apparatus 50 used to process the substrate 22 to deposit the coating 32. Deposition may also be accomplished by sputtering or other operable approach. The deposition apparatus preferably allows a negative voltage potential to be applied during deposition to the substrate 22 relative to the deposition sources. The deposition apparatus 50 includes a chamber 52 having a body 54 and a door 56 that may be opened for access to the interior of the chamber 52 and which is hermetically sealed to the body 54 when the chamber 52 is in operation. The interior of the chamber 52 is controllably evacuated by a vacuum pump 58 operating through a gate valve 60. The vacuum pump 58 includes a mechanical pump and a diffusion pump operating together in the usual manner. The interior of the chamber 52 may controllably backfilled to a partial pressure of a selected gas from a gas source 62 through a backfill valve 64. The gas source typically includes several separately operable gases. The gas source 62 usually includes a source 62a of an inert gas such as argon, a source 62b of nitrogen gas, and a source 62c of a carbon-containing gas such as acetylene, each providing gas selectively and independently through a respective selector valve 65a, 65b, or 65c. Other types of gas can also be provided as desired.

The pressure within the chamber 52 is monitored by a vacuum gage 66, whose output signal is provided to a pressure controller 68. The pressure controller 68 controls the settings of the gate valve 60 and the backfill valve 64 (and, optionally, the selector valves 65), achieving a balance of pumping and backfill gas flow that produces a desired pressure in the chamber 52 and thence pressure reading in the vacuum gage 66. Thus, the gaseous backfilled atmosphere within the chamber 52 is preferably a flowing or dynamic atmosphere.

At least two, and preferably four as shown, linear deposition sources 70 are mounted within the interior of the chamber 52 in a circumferentially spaced-apart manner. In FIG. 4, the four deposition sources are identified as distinct sources 70a, 70b, 70c, and 70d. The four deposition sources 70 are generally rectangular bodies having a greatest rectilinear dimension elongated parallel to a source axis 72 (FIG. 5). This type of deposition source is distinct from either a stationary point source or a point source that moves along the length of the substrate during deposition procedures.

A substrate support 74 is positioned in the chamber 52. The substrate support 74 produces a compound rotational movement of a substrate mounted thereon. The preferred substrate support 74 includes a rotational carriage 76 that rotates about a rotational axis 78, driven by a rotational drive motor 80 below the rotational carriage 76. Mounted on the rotational carriage 76 are at least one and preferably six, as shown, planetary carriages 82. The planetary carriages 82 are rotationally driven about a rotational axis 84 by a gear linkage (not shown) from the rotational drive motor 80. Alternatively, a separate planetary drive motor below the planetary carriages 82 may be used. The speed of the rotational drive motor 80 is controlled by a rotation controller 88.

For deposition processing, an article 40 to be deposited upon is mounted to the planetary carriage 82 with appropriate fixturing such that a long axis of the article, if any, is parallel to the rotational axis 84. That is, as the rotational carriage 76 and the planetary carriage 82 rotate, the article 40 is continuously rotated so that all sides are coated. For commercial operations, multiple articles are typically mounted on each planetary carriage 82 in the manner described, as illustrated for one of the planetary carriages 82.

In the deposition apparatus 50, the long axis of the article 40, if any, the source axis 72, the rotational axis 78, and the rotational axis 84 are all arranged to be approximately parallel to a common axis 90.

The temperature of the articles 40 during deposition is controlled using a heater 92 that extends parallel to the deposition sources 70 on one side of the interior of the chamber 52. The heater 92 is preferably a radiant heater operating with electrical resistance elements. Experience has shown that, due to the rotational movement of the carriages 76 and 82 and the heat retention capacity of the articles 20, the single heater 92 on one side of the chamber 52 provides a sufficiently uniform heating of the substrates. Additional heaters 92 may be used if necessary. The temperature of the substrate articles 40 is monitored by a temperature sensor 94 such as an infrared sensor that views the interior of the chamber. The temperature measured by the sensor 94 is provided to a temperature controller 96 that commands the power output to the heater 92. Acting in this feedback manner, the temperature controller 96 allows the temperature of the substrate articles to be set both before and during the deposition operation. (The articles are also heated to some extent by the deposition process, so that the heater acts as the fine tuning instrument to control the temperature of the articles.) In the preferred processing of steel articles 40 with an applied zirconium or zirconium-compound coating, the articles are heated to a temperature of from about 500° F. to about 850° F.

Figure 6:
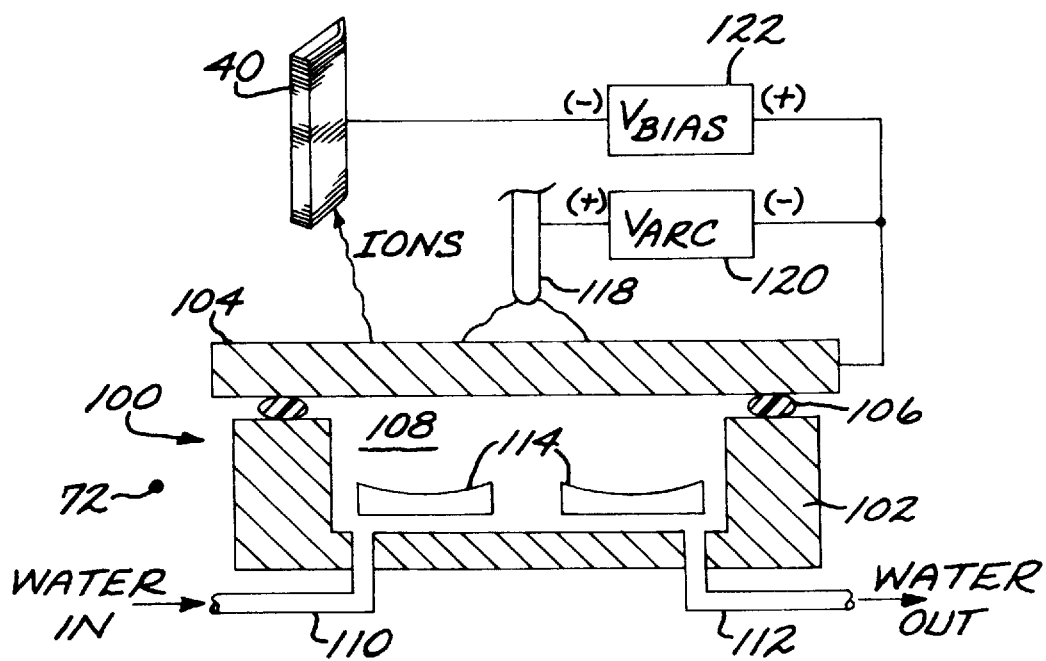
FIG. 6 is a schematic sectional view of a preferred cathodic arc source, taken along lines 6—6 of FIG. 5.

FIG. 6 illustrates a cathodic arc source 100 used in the preferred form of the deposition source 70. (A sputtering source or other operable source may be used instead of the cathodic arc source.) The cathodic arc source 100 includes a channel-shaped body 102 and a deposition target 104. The deposition target 104 is in the form of a plate that is hermetically sealed to the body 102 using an O-ring 106, forming a water-tight and gas-tight hollow interior 108. The interior 108 is cooled with cooling water flowing through a water inlet 110 and a water outlet 112. Two concavely shaped permanent magnets 114 extend parallel to the source axis 72. Positioned above the deposition target 104 exterior to the body 102 is a striker electrode 118. A voltage $V_{ARC}$ is applied between the striker electrode 118 and the deposition target 104 by an arc source power supply 120. $V_{ARC}$ is preferably from about 10 to about 50 volts.

The material that initially forms the deposition target 104 is deposited onto the substrate articles 40, together with, if desired, gas atoms producing anionic species from the atmosphere of the chamber. In the preferred embodiment, the deposition target 104 is made of zirconium (Zr). Other species operable as the deposition target material include metals found in Groups IV—VI of the Periodic Table, including but not limited to vanadium, chromium, titanium, niobium, molybdenum, hafnium, tantalum, and tungsten. Other metals such as aluminum may be used. The deposition target may also be made of alloys or intermetallic compounds.

To accomplish the deposition, an arc is struck between the striker electrode 118 and the deposition target 104, locally heating the deposition target 104 and causing positively charged metallic ions to be ejected from the deposition target 104. (The deposition target 104 is therefore gradually thinned as the deposition proceeds.) The striking point of the arc on the deposition target 104 moves in a racetrack course along the length of the deposition target 104. A negative bias voltage $V_{BIAS}$ is applied between the deposition target 104 and the substrate article 40 by a bias power supply 122, so that the positively charged metallic or intermetallic ions are accelerated toward the article 40.

$V_{BIAS}$ is preferably from about −50 to about −600 volts. The value selected for $V_{BIAS}$ determines the energy of ionic impacts against the surface of the article 40. In a typical case, $V_{BIAS}$ is initially selected to be a relatively large negative voltage, typically about −400 volts, to achieve good adherence of the first coating layer 34 to the article substrate 22. $V_{BIAS}$ is subsequently made less negative, typically to about −50 volts, when the second coating layer 36 and any other overlying hard layers are deposited, to achieve a uniform fine microstructure in the layers.

During the final stages of the deposition of the topmost coating layer, in the preferred embodiment the second coating layer 36, $V_{BIAS}$ is adjusted to a value more negative than about −70 volts and most preferably in the range of from about −70 volts to about −600 volts. This large negative value of $V_{BIAS}$ desirably produces a slight nonuniform roughening of the coated edge 38 and thence the atomic serration and sharpening effect that enhances cutting performance. It is believed that this nonuniform roughening results from backsputtering removal of a small amount of the material of the second coating layer 36 along the coated edge 38, which has a very small radius of curvature and is therefore subject to backsputtering effects. This processing to produce nonuniform roughening is performed for only a few minutes at most, to avoid removal of significant amounts of the second coating layer 36 at other locations.

The cathodic arc source is preferred, but other types of sources such as sputtering sources may also be used.

Figure 7:
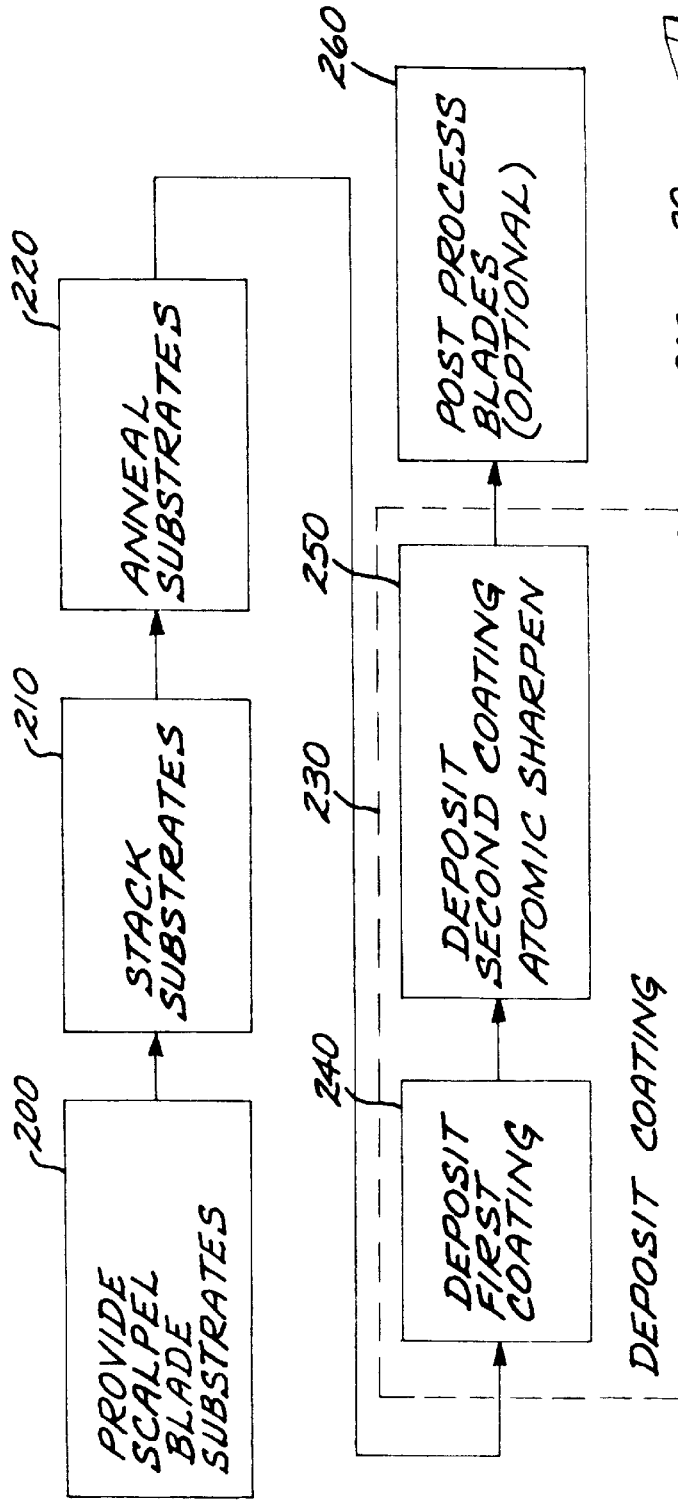
FIG. 7 is a block process flow diagram for a preferred method for practicing the invention.
Figure 8:
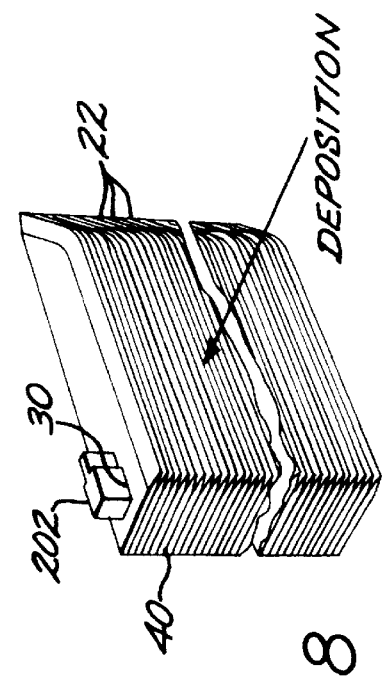
FIG. 8 is a stack of scalpel blades ready for deposition of the coating.

FIG. 7 depicts a preferred approach for preparing the coated scalpel blade 20. This approach has been shown to produce scalpel blades having highly reproducible physical structures and properties. In this approach, a number of the substrates 22 are provided, numeral 200. The substrates 22 are stacked together as shown in FIG. 8, numeral 210, using a post 202 extending through the aligned apertures 30 to align the substrates 22. The stack of aligned substrates 22 is placed into the deposition apparatus 50 and serves as the article 40 to be deposited upon.

The substrates 22 are preferably surgical-grade stainless steel provided in a hardened condition of Rockwell C hardness of at least 54, and typically in the range of from about 54 to about 62. They are annealed using the heater 92, numeral 220, by heating them to a temperature that is typically in the range of from about 800° F. to about 850° F., for a time of from about 45 to about 90 minutes. This annealing reduces the hardness of the stainless steel by at least about 5 points of Rockwell C hardness. In a usual case, the stainless steel is annealed to a Rockwell C hardness of less than about 53, and typically in the range of from about 46 to less than about 53. Most stainless steel scalpel blades are received in a hardness range of from about 54 to about 58 measured on the Rockwell C scale. Annealing them to achieve a reduction of at least about 5 points results in a Rockwell C hardness of the final scalpel blade of from about 46 to less than about 53. However, in some cases the stainless steel scalpel blades may be received with a Rockwell C hardness of from about 58 to about 62. Annealing such scalpel blades to reduce their hardness by at least about 5 points results in a Rockwell C hardness of the final scalpel blade of from about 53 to about 57, which is acceptable for some applications. However, at the present time it is most preferred that the final scalpel blade have a hardness of from about 46 to less than about 53.

It has been known generally to anneal stainless steel, but such annealing has not heretofore been acceptable for scalpel blades whose cutting edges had a small included angle A, of less than about 26 degrees, because the resulting cutting edges of the scalpel blades are too soft for use in cutting procedures. The present approach of coating the scalpel blades with the coating 32 allows the stainless steel to be annealed to a lower hardness and still be operable. The annealing has the important advantageous effect of increasing the ductility and the toughness of the stainless steel substrate of the final scalpel blades 20, and particularly the tapered region 26. The final coated scalpel blades therefore have a combination of toughness of the base substrate material that resists fracture when the scalpel blade impacts bone or other hard material, while at the same time having a very high sharpness (because of the small included angle A, the coating 32, and the sharp coated edge 38) that is retained for an extended period of use during service.

The coating 32 is deposited, numeral 230. The first coating layer 34 is deposited, numeral 240, of a metal which is preferably, but not necessarily, the same as the metallic component of the overlying second coating layer 36. The first coating layer 34 aids in adhering the overlying layer(s) to the surface of the substrate 22. The first coating layer 32 is preferably quite thin, on the order of from about 100 Angstroms to about 600 Angstroms thick. The first coating layer 34 is deposited by backfilling the deposition chamber with a small partial pressure of about 5 microns of an inert gas such as flowing argon (flowing at a rate of about 200–450 standard cubic centimeters per minute (sccm) in the apparatus used by the inventor), and then depositing zirconium or a metallic alloy thereof from the deposition target 104 with $V_{BIAS}$ about −400 volts. Because the argon does not chemically react with the zirconium, the first layer 34 is metallic zirconium or a metallic alloy thereof The first layer 34 is deposited in about 6 minutes in a typical case.

The second coating layer 36 is deposited, numeral 250, overlying the first coating layer 34. In the most preferred embodiment, the second layer 36 is zirconium nitride (ZrN), which is deposited by backfilling the deposition chamber with a small partial pressure of about 5 microns of flowing nitrogen (flowing at a rate of about 150–500 sccm in the inventors' apparatus), and then depositing zirconium from the deposition target 104 with $V_{BIAS}$ about −50 volts initially. The zirconium ions combine with the nitrogen anions to produce the ZrN coating in the second coating layer 36. The second coating layer 36 is of a thickness such that the total thickness of the coating 32 is from about 0.1 to about 2.5 micrometers.

In the latter stage of the second coating deposition step 250, $V_{BIAS}$ is preferably reduced to a value that is more negative than −70 volts, is more preferably in the range of from about −70 volts to about −600 volts, and is most preferably about −400 volts. Deposition of the coating, in the preferred case zirconium nitride, is continued at this voltage. The result is that the coated edge 38 has a substantially increased sharpness, as compared with its sharpness if $V_{BIAS}$ were maintained in the −50 volt range throughout the entire second coating deposition step 250. The operability of this enhanced sharpening is not dependent upon a knowledge of the exact mechanism, but it is believed that the coated edge 38 is atomically serrated and thence atomically sharpened by a backsputtering mechanism in this latter stage of the step 250. In a typical case of depositing a coating 32 that is about 0.3 micrometers thick, the deposition in the second coating deposition step 250 proceeds with $V_{BIAS}$ in the −50 volt range for about 4–8 minutes and with $V_{BIAS}$ in the range of from about −70 to about −600 volts, most preferably about −400 volts, for about 30 seconds to about 3 minutes. For thicker coatings 32, the duration of the portion of the coating step 250 with $V_{BIAS}$ in the −50 volt range is lengthened, typically to about 60–90 minutes for a 2½ micrometer coating 32. The duration of the portion of the coating step 250 with $V_{BIAS}$ greater than about −70 volts is preferably not significantly lengthened, as some regions of the coating may be unduly thinned by backsputtering.

The scalpel blade 20 may be post processed as necessary for particular applications, numeral 260. Such post processing may include, for example, additional sharpening of the coated edge 38 by lapping, or application of a further protective coating such as a polytetrafluoroethylene layer over the coating 32.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A coated scalpel blade, comprising:
    a substrate having a body and a tapered region with a cutting edge thereon, the substrate being made of steel hardened to a Rockwell C hardness of at least 54 and then annealed to a Rockwell C hardness of from about 46 to less than about 53; and
    a coating overlying the tapered region, the coating having a thickness of from about 0.1 to about 2.5 micrometers and comprising
        a first coating layer of a first metal, and
        a second coating layer overlying the first coating layer, the second coating layer comprising a chemical combination of a second metal selected from the group consisting of vanadium, chromium, zirconium, titanium, niobium, molybdenum, hafnium, tantalum, and tungsten, and combinations thereof, and a nonmetal selected from the group consisting of nitrogen and carbon, and combinations thereof, the coated scalpel blade having a coated edge thereon.

2. The coated scalpel blade of claim 1, wherein the coating has a thickness of from about 0.1 to about 1.0 micrometer.

3. The coated scalpel blade of claim 1, wherein the first coating layer comprises zirconium and the second coating layer comprises zirconium nitride.

4. The coated scalpel blade of claim 1, wherein the first metal and the second metal are the same metal.

5. The coated scalpel blade of claim 1, wherein the tapered region has an included angle of from about 10 to about 25 degrees.

6. The coated scalpel blade of claim 1, wherein the coated edge is atomically serrated.

7. The coated scalpel blade of claim 1, wherein the substrate is surgical-grade stainless steel.

8. A coated scalpel blade, comprising:
    a substrate having a body and a tapered region with a cutting edge thereon, the substrate being made of steel initially hardened to a Rockwell C hardness of at least 54 and then annealed to reduce the hardness by at least about 5 points on the Rockwell C hardness scale; and
    a coating overlying the tapered region, the coating having a thickness of from about 0.1 to about 2.5 micrometers and comprising
        a first coating layer of a first metal, and
        a second coating layer overlying the first coating layer, the second coating layer comprising a chemical combination of a second metal selected from the group consisting of vanadium, chromium, zirconium, titanium, niobium, molybdenum, hafnium, tantalum, and tungsten, and combinations thereof, and a nonmetal selected from the group consisting of nitrogen and carbon, and combinations thereof, the coated scalpel blade having a coated edge thereon.

9. The coated scalpel blade of claim 8, wherein the first coating layer comprises zirconium and the second coating layer comprises zirconium nitride.

10. A method for preparing a coated scalpel blade, comprising the steps of:
    providing a substrate in a shape of a scalpel blade having a body and a tapered region with a cutting edge thereon, the substrate being made of steel hardened to a Rockwell C hardness of at least 54; thereafter
    annealing the substrate to reduce its hardness by at least about 5 points on the Rockwell C scale; and
    depositing a coating from a deposition source onto at least the tapered region of the substrate, the coating having a thickness of from about 0.1 to about 2.5 micrometers, the step of depositing comprising the steps of
        first depositing a first coating layer of a first metal, and thereafter
        second depositing a second coating layer overlying the first coating layer, the second coating layer comprising a chemical combination of a second metal selected from the group consisting of vanadium, chromium, zirconium, titanium, niobium, molybdenum, hafnium, tantalum, and tungsten, and combinations thereof, and a nonmetal selected from the group consisting of nitrogen and carbon, and combinations thereof,
        wherein the step of second applying includes the step of
            applying a voltage more negative than about −70 volts to the substrate relative to the deposition source.

11. The method of claim 10, wherein the step of annealing and the step of depositing are performed in the same apparatus.

12. The method of claim 10, wherein the deposition source is a cathodic arc deposition source.

13. The method of claim 10, wherein the step of providing includes the step of
    providing a plurality of substrates, and the step of depositing includes the steps of stacking the plurality of substrates with their bodies adjacent to each other and their edges facing in a common direction, and orienting the edges facing toward the deposition source.

14. The method of claim 10, wherein the step of depositing includes the step of first depositing the first coating layer comprising zirconium, and second depositing the second coating layer comprising zirconium nitride.

15. The method of claim 10, wherein the coating has a thickness of from about 0.1 to about 1.0 micrometer.

16. The method of claim 10, wherein the coating has a thickness of about 0.3 micrometer.

17. The method of claim 10, wherein the first metal and the second metal are the same metal.

18. The method of claim 10, wherein the tapered region has an included angle of from about 10 to about 25 degrees.

19. The method of claim 10, wherein the substrate is surgical-grade stainless steel.

20. The method of claim 10, wherein the step of annealing produces a substrate having a Rockwell C hardness of from about 46 to less than about 53.

* * * * *